(12) United States Patent
Tabata

(10) Patent No.: US 8,435,953 B2
(45) Date of Patent: May 7, 2013

(54) SUSTAINED RELEASE COMPOSITION CONTAINING SDF-1

(75) Inventor: Yasuhiko Tabata, Uji (JP)

(73) Assignees: Yasuhiko Tabata, Uji-shi, Kyoto (JP); Ono Pharmaceutical Co., Ltd., Osaka-shi, Osaka (JP)

( * ) Notice: Subject to any disclaimer, the term of this patent is extended or adjusted under 35 U.S.C. 154(b) by 143 days.

(21) Appl. No.: 12/741,694

(22) PCT Filed: Nov. 6, 2008

(86) PCT No.: PCT/JP2008/003204
§ 371 (c)(1), (2), (4) Date: May 6, 2010

(87) PCT Pub. No.: WO2009/060608
PCT Pub. Date: May 14, 2009

(65) Prior Publication Data
US 2010/0267612 A1 Oct. 21, 2010

(30) Foreign Application Priority Data
Nov. 7, 2007 (JP) .................. 2007-289598

(51) Int. Cl.
A61K 38/18 (2006.01)
A61K 8/65 (2006.01)
A61K 9/52 (2006.01)
C07K 14/525 (2006.01)

(52) U.S. Cl.
USPC ........ 514/21.3; 514/13.3; 514/16.7; 514/774; 514/963; 514/964; 530/300; 530/354; 424/492

(58) Field of Classification Search ............. None
See application file for complete search history.

(56) References Cited

U.S. PATENT DOCUMENTS

| | | | |
|---|---|---|---|
| 6,297,337 B1 * | 10/2001 | Marchant et al. ............ | 526/328 |
| 6,831,058 B1 | 12/2004 | Ikada et al. | |
| 2004/0253294 A1 | 12/2004 | Tabata | |
| 2005/0271697 A1 | 12/2005 | Litvack | |
| 2009/0285785 A1 | 11/2009 | Jimi et al. | |

FOREIGN PATENT DOCUMENTS

| | | |
|---|---|---|
| WO | 94/27630 A1 | 12/1994 |
| WO | 03/007982 A1 | 1/2003 |
| WO | 2004/030691 A1 | 4/2004 |
| WO | 2005/120549 A2 | 12/2005 |
| WO | 2006/030887 A1 | 3/2006 |
| WO | 2007/080898 A1 | 7/2007 |

OTHER PUBLICATIONS

Kato et al. Synthesis of bioadhesive gelatin hydrogels through modification with carboxylic acids. Koen Yoshishu—Nippon Setchaku Gakkai Nenji Taikai (2000), 38th, 69-70.*
Franz et al. Stem-cell homing and tissue regeneration in ischaemic cardiomyopathy. Lancet. Aug. 30, 2003;362(9385):675-6.*
Iwakura et al. Intramyocardial sustained delivery of basic fibroblast growth factor improves angiogenesis and ventricular function in a rat infarct model. Heart Vessels. May 2003;18(2):93-9.*
Kato et al. Synthesis of bioadhesive gelatin hydrogels through modification with carboxylic acids. Koen Yoshishu—Nippon Setchaku Gakkai Nenji Taikai (2000), 38th, 69-70, English translation.*
Tan et al. Stromal cell-derived factor-1 enhances pro-angiogenic effect of granulocyte-colony stimulating factor. Cardiovasc Res. Mar. 1, 2007;73(4):823-32. Epub Dec. 23, 2006.*
Yamaguchi et al. Stromal cell-derived factor-1 effects on ex vivo expanded endothelial progenitor cell recruitment for ischemic neovascularization. Circulation. Mar. 11, 2003;107(9):1322-8.*
International Search Report issued on Dec. 9, 2008 in International Application No. PCT/JP2008/003204.
Ceradini, Daniel J. et al., "Progenitor cell trafficking is regulated by hypoxic gradients through HIF-1 induction of SDF-1", Nature Medicine, vol. 10, No. 8, Aug. 2004, pp. 858-864.
Askari, Arman T. et al., "Effect of stromal-cell-derived factor 1 on stem-cell homing and tissue regeneration in ischaemic cardiomyopathy", The Lancet, vol. 362, Aug. 30, 2003, pp. 697-703.
Hiasa, Ken-ichi MD et al., "Gene Transfer of Stromal Cell-Derived Factor-1 α Enhances Ischemic Vasculogenesis and Angiogenesis via Vasular Endothelial Growth Factor/Endothelial Nitric Oxide Synthase-Related Pathway" Next-Generation Chemokine Therapy for Therapeutic Neovascularization, Circulation, vol. 109, 2004, pp. 2454-2461.

* cited by examiner

*Primary Examiner* — David Romeo
(74) *Attorney, Agent, or Firm* — Fitch, Even, Tabin & Flannery, LLP

(57) ABSTRACT

An object of the present invention is to provide a sustained release composition containing SDF-1. The present invention provides a sustained release composition containing (1) SDF-1 and (2) a hydrogel containing modified gelatin having a carboxyl group and/or a sulfo group. Since the composition can release SDF-1, a chemokine which is a capable of promoting accumulation of vascular progenitor cells in vivo, in the sustained manner, it can be useful for treatment and/or suppression of symptom progression of ischemic disease or bone disease, as pharmaceutical preparations in various formulations.

18 Claims, 3 Drawing Sheets

SUSTAINED RELEASE COMPOSITION CONTAINING SDF-1

CROSS REFERENCE TO RELATED APPLICATIONS

This application is a U.S. National Stage entry of International Application No. PCT/JP2008/003204 filed on Nov. 6, 2008, which claims priority to Japanese Application No. 2007-289598, filed on Nov. 7, 2007. The complete disclosures of the referenced international and priority application are incorporated herein by reference.

TECHNICAL FIELD

The present invention relates to a sustained release composition containing SDF-1 which is a type of chemokine. More specifically, the present invention relates to a sustained release composition containing SDF-1 and a succinylated gelatin hydrogel or a sulfoacetylated gelatin hydrogel.

BACKGROUND ART

SDF-1 (stromal cell-derived factor-1) is a protein which belongs to a CXC chemokine family containing conserved 4 cysteine residues and is recognized to have a plurality of isoforms including α, β, and γ. From 1993 to 1994, SDF-1 was discovered as a novel secretory protein produced by bone marrow stromal cells and furthermore as a protein having a growth promoting function for B-lymphoid progenitor cell clones. Thereafter in 1996, it was revealed that SDF-1 is a protein which inhibits a receptor necessary for invasion of human immunodeficiency virus (HIV) into a host cell.

It has been known that SDF-1-deficient mice die immediately after birth and present abnormalities in hematopoiesis in the bone marrow, formation of the interventricular septum or neural tissue formation. Furthermore, it has been revealed that the SDF-1 receptor is CXCR4 and the SDF-1 first among the chemokines forms a ligand-receptor relationship together with CXRC4.

One of the physiological actions of SDF-1 is a angiogenesis-inducing action. The angiogenesis-inducing action of SDF-1 is based on an action of recruiting vascular progenitor cells to an ischemic site and has been attracting attention in being a different mechanism from the angiogenesis-inducing activity due to growth factors having an intrinsic angiogenesis-inducing activity such as basic fibroblast growth factor (bFGF) or vascular endothelial growth factor (VEGF).

To date, documents which link SDF-1 to angiogenesis have reported that SDF-1 production is induced by hypoxia-inducible factor 1 (HIF-1) produced at the ischemic site using dorsal skin-lift animal models and consequently accumulation of vascular progenitor cells at the ischemic site is caused (for example, see Nature Medicine, volume 10(8), pages 858-864 (2004)). Furthermore, it has been reported that transplantation of fibroblasts which have been genetically modified to produce SDF-1 into sites of myocardial infarction accumulates bone marrow-derived vascular progenitor cells in the infarction sites and additionally improves the cardiac function (for example, see Lancet (volume 362, pages 697-703 (2003)). It has also been reported that administration of SDF-1 genes to ischemia sites of inferior limb had resulted in observation of angiogenesis and in an increase in the blood flow volume (for example, refer to Circulation, volume 109, pages 2454-2461, (2004)).

Examples of sustained release compositions containing growth factors having a angiogenesis activity include a formulation combining bFGF with a crosslinked gelatin gel (for example, see International Publication No. WO 94/27630) or a formulation combining a hepatocyte growth factor (HGF) with a gelatin hydrogel (for example, see International Publication No. WO 2003/007982).

However, both of the above prior techniques do not teach continuous external administration of SDF-1, and there has been no safe sustained release composition which enables effective manifestation of a pharmacological action of SDF-1 and can be administered to a living body.

DISCLOSURE OF THE INVENTION

Problems to be Solved by the Invention

Generally, when a protein is administered to a living body in an aqueous solution form, no desired biological effect can be obtained since the protein is rapidly degraded. In order to solve such a problem, various sustained release techniques have been investigated in recent years and several sustained release compositions containing physiologically active substances have been reported. However, due to diverse structures and diverse pharmacological actions of proteins, it is extremely difficult to design preparations which can effectively impart only a specific pharmacological action of a certain protein to a living body. Since the working mechanism of SDF-1 differs from previously known growth factors having a angiogenesis activity and there is no example of continuous external administration to a living body, it is completely unclear regarding what local concentration (or blood concentration) for what duration of action would induce a pharmacological effect desirable for a living body or what sustained release carrier could be used in order to stabilize SDF-1 in vivo.

That is to say, an object of the present invention is to provide a sustained release composition containing SDF-1, suitable for inducing a local physiological action, and enabling safe administration to a living body.

Means for Solving the Problems

On the basis of diligent investigations using numerous sustained release carriers, the present inventors have found that a succinylated gelatin hydrogel or a sulfoacetylated gelatin hydrogel exhibits excellent SDF-1 sustained release effects and that when each hydrogel is administered to a living body together with SDF-1, a conspicuously excellent angiogenesis-inducing effect is obtained which is not observed when using other sustained release carriers. The present inventors conducted further investigations based on the above insight and thereby completed the present invention.

Thus, the present invention provides:
[1] A sustained release composition containing (1) SDF-1 and (2) a hydrogel containing modified gelatin having a carboxyl group and/or a sulfo group;
[2] The sustained release composition according to [1], wherein the hydrogel containing modified gelatin having a carboxyl group and/or a sulfo group is a succinated gelatin hydrogel, a sulfoacetylated gelatin hydrogel or a mixture thereof in an arbitrary ratio;
[3] The sustained release composition according to [2], wherein the succinylated gelatin hydrogel, the sulfoacetylated gelatin hydrogel or the mixture thereof in an arbitrary ratio is produced by crosslinking succinylated gelatin, sulfoacetylated gelatin or a mixture thereof in an arbitrary ratio at the isoelectric point of about 4.5 to about 5.0 using a crosslinking agent;

[4] The sustained release composition according to [2], wherein the succinylated gelatin hydrogel, the sulfoacetylated gelatin hydrogel or the mixture thereof in an arbitrary ratio is produced by crosslinking succinylated gelatin, sulfoacetylated gelatin or a mixture thereof in an arbitrary ratio at the modification ratio of about 15% to about 30% using a crosslinking agent;

[5] The sustained release composition according to [2], wherein the succinylated gelatin hydrogel, the sulfoacetylated gelatin hydrogel or the mixture thereof in an arbitrary ratio is produced by crosslinking succinylated gelatin, sulfoacetylated gelatin or a mixture thereof in an arbitrary ratio which has an average molecular weight of about 90,000 to about 110,000 using a crosslinking agent;

[6] The sustained release composition according to [1], wherein SDF-1 is SDF-1α, SDF-1β or a mixture thereof in an arbitrary ratio;

[7] The sustained release composition according to [1] for injection, transnasal administration, transdermal administration, rectal administration or implantation;

[8] The sustained release composition according to [7] for implantation;

[9] The sustained release composition according to [8], having a water content ratio of from about 95% to about 98%;

[10] The sustained release composition according to [8], wherein SDF-1 is released over at least 1 week;

[11] The sustained release composition according to [10], wherein SDF-1 is released over about 1 month to about 2 months;

[12] The sustained release composition according to [7], wherein the injection is subcutaneous microsphere injection;

[13] The sustained release composition according to [1] for treatment and/or suppression of symptom progression of ischemic disease or bone disease;

[14] A method for producing the sustained release composition according to [8], which includes the steps of:
 (1) mixing an aqueous solution of modified gelatin having a carboxyl group and/or a sulfo group with an aqueous solution of a crosslinking agent to prepare a hydrogel containing modified gelatin having a carboxyl group and/or a sulfo group;
 (2) freeze-drying the hydrogel containing modified gelatin obtained in step (1); and
 (3) bringing an aqueous solution of SDF-1 into contact with the freeze-dried body of the hydrogel containing modified gelatin obtained in step (2) to thereby make the hydrogel contain modified gelatin support SDF-1.

[15] The production method according to [14], wherein about 10 mmol to about 50 mmol of SDF-1 relative to 1 mol of modified gelatin having a carboxyl group and/or a sulfo group is supported in the hydrogel containing modified gelatin having a carboxyl group and/or a sulfo group;

[16] A pharmaceutical preparation containing the sustained release composition according to [1];

[17] The pharmaceutical preparation according to [16] for treatment and/or suppression of symptom progression of ischemic disease or bone disease;

[18] A method for treatment and/or suppression of symptom progression of ischemic disease or bone disease, comprising administering an effective amount of the pharmaceutical preparation according to [16] to a mammal;

[19] Use of the pharmaceutical preparation according to [16] for the production of an agent for treatment and/or suppression of symptom progression of ischemic disease or bone disease; and

[20] A method for sustained releasing SDF-1 in vivo, comprising a step of making a hydrogel containing modified gelatin having a carboxyl group and/or a sulfo group support SDF-1.

Effects of the Invention

Since the present invention enables chemokine SDF-1 to be released in vivo in a sustained manner, it enables SDF-1 to induce angiogenesis or reproduction of various tissues including cartilage, muscle or dermal tissues by, for example, injection, nasal administration, transdermal administration, rectal administration or implantation of the composition. Also, for example, the invention enables treatment and/or suppression of symptom progression of ischemic disease or bone disease. The hydrogel containing modified gelatin having a carboxyl group and/or a sulfo group used in the composition of the present invention improves the in-vivo stability of SDF-1 and therefore can also be useful as an in-vivo stabilizing agent for SDF-1.

Figure 1:
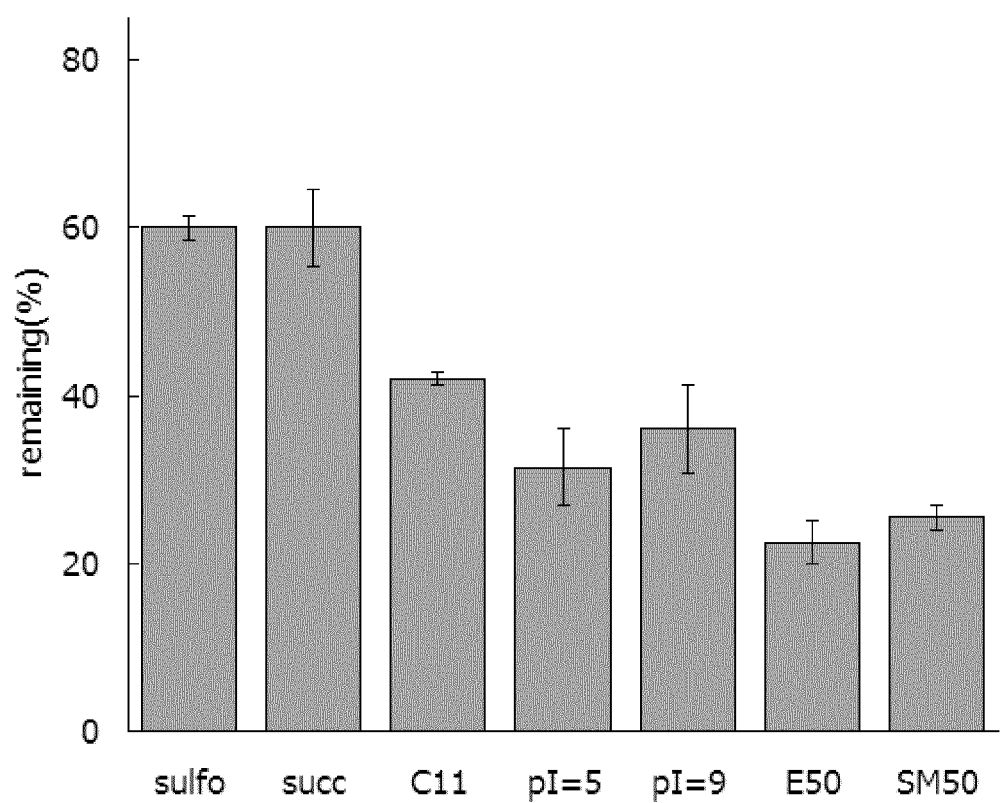
FIG. 1 shows the sustained release of SDF-1 from various gelatin hydrogels.

The present specification includes the contents described in the specification of Japanese Patent Application No. 2007-289598 filed Nov. 7, 2007, which is the basis of priority of the present invention.

BEST MODE FOR CARRYING OUT THE INVENTION

In the present invention, SDF-1 may include isoforms and mature forms thereof such as SDF-1β, SDF-1γ, SDF-1δ, SDF-1ε and SDF-1φ in addition to SDF-1α or a mature form thereof, or a mixture thereof in an arbitrary ratio or the like. SDF-1 preferred in the present invention includes SDF-1α, SDF-1β, a mixture thereof in an arbitrary ratio or the like. SDF-1 may also be termed CXCL-12 or PBSF.

In the present invention, as long as SDF-1 has activity as a chemokine, SDF-1 may be substituted, deleted and/or added by one or plural amino acid(s) in the amino acid sequence. Similarly, it may be substituted, deleted and/or added by sugar chain. SDF-1 may form a salt (preferably, an acid addition salt) with a physiologically acceptable acid (for example, an inorganic acid or an organic acid) or a base (for example, an alkali metal salt). Examples of the salt include a salt with an inorganic acid (for example, hydrochloric acid, phosphoric acid, hydrobromic acid, or sulfuric acid) and a salt with an organic acid (for example, acetic acid, formic acid, propionic acid, fumaric acid, maleic acid, succinic acid, tartaric acid, citric acid, malic acid, oxalic acid, benzoic acid, methanesulfonic acid, or benzenesulfonic acid).

The type of SDF-1 is not limited in the present invention. SDF-1 used in the present invention may be derived from mammals such as human, or non-human animals such as monkey, sheep, cow, horse, pig, dog, cat, rabbit, rat, or mouse. Normally, target species may be selected for application of "a sustained release composition containing (1) SDF-1 and (2) a hydrogel containing modified gelatin having a carboxyl group and/or a sulfo group" as disclosed in the present invention (hereafter may be sometimes abbreviated to the "composition of the present invention"). For example, when the composition of the present invention is applied to human, the composition of the present invention may be produced using human SDF-1 (for example, SDF-1α (GeneBank Accession No. NP_954637) or SDF-1β (GeneBank Accession No. NP_000600)).

In the present invention, SDF-1 may be purified to a level at which the action of SDF-1 is not inhibited by other contaminants. Preferably, SDF-1 may be purified to be usable as a pharmaceutical preparation.

In the present invention, SDF-1 may be obtained from natural sources or produced by a genetic engineering technique. When obtained from natural sources, SDF-1 may be extracted from various organs such as the spleen of mammals such as human or non-human animal (for example, monkey, sheep, cow, horse, dog, cat, rabbit, rat, or mouse), in which SDF-1 is already known to exist. To give a specific example of an organ in which SDF-1 is known to exist, for example, SDF-1 is known to be present in a large amount in organs in which tumor cells expressing CXCR4, a SDF-1 receptor, transfer with high frequency. On the other hand, when produced by a genetic engineering technique, a gene coding SDF-1 from a mammal such as human or non-human animals (for example, monkey, sheep, cow, horse, pig, dog, cat, rabbit, rat, or mouse) is incorporated into a suitable vector, which is introduced into a suitable host cell for transformation, to thereby be able to obtain the target recombinant SDF-1 from a culture supernatant of the transformant. The host cell herein is not limited and various host cells such as $E.$ $coli$, yeast cells, various insect cells such as silkworm cells and various animal cells, which have been normally used in the genetic engineering techniques, may be used.

In the present invention, the "hydrogel containing modified gelatin having a carboxyl group and/or a sulfo group" (hereafter may be simply abbreviated to the "hydrogel used in the present invention") means a hydrogel produced using "modified gelatin having a carboxyl group and/or a sulfo group". Herein, the "modified gelatin having a carboxyl group and/or a sulfo group" (hereafter, may be simply abbreviated to the "modified gelatin used in the present invention") may be gelatin in which a carboxyl group and/or a sulfo group is externally introduced into a gelatin molecule and may have any other groups in addition to a carboxyl group and/or a sulfo group. The carboxyl group and/or the sulfo group may directly bond to the gelatin molecule, or the carboxyl group and/or the sulfo group may not be directly bonded to the gelatin molecule. Furthermore, the number of carboxyl groups and/or sulfo groups introduced into the gelatin molecule is not particularly limited. The number of carboxyl groups and/or sulfo groups introduced into the gelatin molecule can be represented by an index referred to as the "modification ratio". The "modification ratio" represents the ratio of the number of carboxyl groups and/or sulfo groups introduced into the amino groups in the gelatin molecule to the total number of amino groups in the gelatin molecule used as a starting material. In other words, if when the gelatin molecule used as a starting material has 100 amino groups, the number of carboxyl groups and/or sulfo groups introduced into the amino groups is 10, the modification ratio is 10%. In the present specification, the carboxyl group means "—COOH" or "—COO$^-$", a deprotonated form thereof, and the sulfo group means "—SO$_3$H" or "—SO$_3^-$", a deprotonated form thereof.

The "modified gelatin used in the present invention" can be produced by acylating gelatin as a raw material using a reagent for introducing a carboxyl group and/or a sulfo group. This acylation reaction is known and examples thereof include (1) a method using a condensing agent, (2) a method using a (mixed) acid anhydride, and (3) a method using an acyl halide. These methods (1) to (3) will be specifically described in the following.

(1) The method using a condensing agent is conducted, for example, by reacting carboxylic acid (for example, aliphatic carboxylic acid substituted with a carboxy group, such as succinic acid, oxalic acid, aliphatic carboxylic acid substituted with a sulfo group, or sulfoacetic acid) with gelatin at about 0° C. to about 40° C. in a solvent (for example, water, dimethyl sulfoxide, N,N-dimethylformamide, ethylene glycol monoethyl ester, tetrahydrofuran, methanol or ethanol alone, or a mixed solvent thereof in an arbitrary ratio) or without a solvent in the presence or absence of a base (for example, pyridine, triethylamine, N,N-dimethylaniline, N,N-dimethylaminopyridine, or diisopropylethylamine), in the presence or absence of a buffer solution (for example, a phosphate buffer solution) using a condensing agent (for example, 1,3-dicyclohexylcarbodiimide (DCC), 1-ethyl-3-[3-(dimethylamino)propyl]carbodiimide (EDC), 1,1'-carbonyldiimidazole (CDI), 2-chloro-1-methylpyridiniumiodine, 1-propylphosphonic acid cyclic anhydride or (1-propanephosphonic acid cyclic anhydride, PPA)) with or without using 1-hydroxybenztriazole (HOBt).

(2) The method using a (mixed) acid anhydride is conducted, for example, by reacting carboxylic acid (for example, aliphatic carboxylic acid substituted with a carboxy group such as succinic acid, oxalic acid, aliphatic carboxylic acid substituted with a sulfo group, or sulfoacetic acid) with an acid halide (for example, pivaloyl chloride, p-toluenesulfonyl chloride, or methanesulfonyl chloride) or an acid derivative (for example, ethyl chloroformate or isobutyl chloroformate) at about −20° C. to about 40° C. in an organic solvent (for example, chloroform, dichloromethane, diethylether, or tetrahydrofuran) or without a solvent in the presence of a base (for example, pyridine, triethylamine, N,N-dimethylaniline, N,N-dimethylaminopyridine, or diisopropylethylamine), and reacting the resultant mixed acid anhydride or a commercially available acid anhydride (for example, succinic anhydride, maleic anhydride, or phthalic anhydride) with gelatin at about 0° C. to about 40° C. in a solvent (for example, water, dimethyl sulfoxide, N,N-dimethylformamide, ethylene glycol monoethyl ester, tetrahydrofuran, methanol or ethanol alone, or a mixed solvent thereof in an arbitrary ratio) in the presence or absence of a buffer solution (for example, a phosphate buffer solution).

(3) The method using an acyl halide is conducted, for example, by reacting carboxylic acid (for example, aliphatic carboxylic acid substituted with a carboxy group such as succinic acid, oxalic acid, aliphatic carboxylic acid substituted with a sulfo group, or sulfoacetic acid) with an acid-halidation agent (for example, oxalyl chloride or thionyl chloride) at about −20° C. to a reflux temperature in an organic solvent (for example, chloroform, dichloromethane, diethylether, or tetrahydrofuran) or without a solvent, and reacting the resultant acyl halide or a commercially available acyl halide (for example, succinic acid monochloride or sulfoacetyl chloride) with gelatin at a temperature of about 0° C. to about 40° C. in a solvent (for example, water, dimethyl sulfoxide, N,N-dimethylformamide, ethylene glycol monoethyl ester, tetrahydrofuran, methanol or ethanol alone, or a mixed solvent thereof in an arbitrary ratio) in the presence of a base (for example, pyridine, triethylamine, N,N-dimethylaniline, N,N-dimethylaminopyridine, or diisopropylethylamine), in the presence or absence of a buffer solution (for example, a phosphate buffer solution). The method may be also conducted by reacting the resultant acyl halide or a commercially available acyl halide (for example, succinic acid monochloride or sulfoacetyl chloride) with gelatin at about 0° C. to about 40° C. in a solvent (for example, water, dimethyl sulfoxide, N,N-dimethylformamide, ethylene glycol monoethyl ester, tetrahydrofuran, methanol or ethanol alone, or a mixed solvent thereof in an arbitrary ratio) using an aqueous alkali solution (for example, an aqueous sodium hydrogen carbonate solution or an aqueous sodium hydroxide solution) in the presence or absence of a buffer solution (for example, a phosphate buffer solution).

The "modified gelatin used in the present invention" produced using the above method may be dialyzed, ultrafiltrated, purified by molecular weight sieving or the like, or freeze-dried as desired.

Gelatin used as the starting material for production of the "modified gelatin used in the present invention" may be obtained from a natural source, or may be obtained by fermentation using microbes, chemical synthesis or genetic recombination operations. It is also possible to use a suitable mixture of these materials above. Natural gelatin may be obtained by denaturalizing collagen derived from each collected site in various animals such as human, mammals (for example, a cow and a pig), fish (for example, tilapia, sea bream, tuna, catfish and a shark) and birds (for example, a chicken and an ostrich) through a variety of treatments such as alkali hydrolysis, acid hydrolysis, or enzymolysis.

Preferred examples of the "modified gelatin used in the present invention" include succinylated gelatin and sulfoacetylated gelatin. The succinylated gelatin means the gelatin in which one or more arbitrary amino group(s) ($-NH_2$) in a gelatin molecule as a raw material have been converted into carboxyethylcarbonylamino group(s) ($-NH-C(=O)-CH_2-CH_2-COOH$). The sulfoacetylated gelatin means the gelatin in which one or more arbitrary amino group(s) ($-NH_2$) in a gelatin molecule as a raw material have been converted into sulfomethylcarbonylamino group(s) ($-NH-C(=O)-CH_2-SO_3H$). The succinylated gelatin and the sulfoacetylated gelatin can be produced by the above methods. More specifically, the succinylated gelatin can be produced by adding dropwise succinic anhydride dissolved in dehydrated dimethyl sulfoxide to gelatin dissolved in dehydrated dimethyl sulfoxide and reacting the mixture at about 37° C. for about 0.5 hours to about 24 hours. Subsequently, the obtained gelatin may further be dialyzed and lyophilized as desired. The sulfoacetylated gelatin can be produced by adjusting the pH adding dropwise sulfoacetic acid dissolved in an aqueous buffer solution to gelatin dissolved in an aqueous buffer solution and subsequently adding thereto 1-ethyl-3-[3-(dimethylamino)propyl]carbodiimide (EDC) hydrochloric acid salt, and reacting the mixture at about 37° C. for about 18 hours. Subsequently, the obtained gelatin may further be dialyzed and lyophilized as desired. The introduction ratio(modification ratio) of carboxyl groups or sulfo groups into the "modified gelatin used in the present invention" can be adjusted within a range from about 5% to 80% by variously varying the reaction time and the concentration of a reaction reagent in the production of the "modified gelatin used in the present invention".

As will be described in the production method later, the composition of the present invention can be produced in various manners in accordance with the purposes (administration site, the level of sustained release(for example, the period of SDF-1 release and the speed of release), and the like). Specifically, examples of the composition of the present invention which releases SDF-1 over about 2 weeks by in vivo implant administration include the composition of the present invention as shown in the following examples. Taking said composition as an example, to produce the composition of the present invention which releases SDF-1 over about 2 weeks by implant administration in vivo, it is preferred that any one of the three properties (A), (B) and (C) described below, preferably any two properties, and more preferably all three properties are imparted to the succinylated gelatin or the sulfoacetylated gelatin which is preferable as the "modified gelatin used in the present invention"; (A) an isoelectric point of about 4.5 to about 5.0; (B) a modification ratio of about 15% to about 30% (preferably, when using succinylated gelatin, about 25% to about 30%, and when using sulfoacetylated gelatin, about 20%); and (C) an average molecular weight of about 90,000 to about 200,000 (preferably about 90,000 to about 110,000, and more preferably about 100,000). As seen in examples described later, the compositions of the present invention produced using the succinylated gelatin or the sulfoacetylated gelatin which fulfills all three conditions exhibit excellent effects coinciding with purposes in sustained release of SDF-1. The isoelectric point, the modification ratio and the average molecular weight can be all measured by a known method. The average molecular weight of the obtained "modified gelatin used in the present invention" can be calculated based on the average molecular weight of gelatin used as a starting material and the modification ratio. In addition to the above properties, it is preferred that, for example, the pH satisfies a condition of about 4 to about 6. Use of the composition of the present invention produced using the resulting gelatin as an injection solution is facilitated by providing conditions such as that the "modified gelatin used in the present invention" has a pH of about 4 to about 6.

Preferred examples of the "hydrogel used in the present invention" include hydrogels produced using the preferred "modified gelatin used in the present invention" described above, namely, the succinylated gelatin hydrogel and the sulfoacetylated gelatin hydrogel. A mixture of the succinylated gelatin hydrogel and the sulfoacetylated gelatin hydrogel in an arbitrary ratio is also preferred.

The "hydrogel used in the present invention" can be produced by subjecting the above "modified gelatin used in the present invention" to a known reaction. For example, the hydrogel can be produced by crosslinking the "modified gelatin used in the present invention" using a crosslinking agent (for example, glutaraldehyde, water-soluble carbodiimide such as 1-ethyl-3-[3-(dimethylamino)propyl]carbodiimide (EDC), propylene oxide, a diepoxy compound, or a condensing agent for forming a chemical bond between a hydroxyl group, a carboxyl group, an amino group, a thiol group, an imidazole group or the like), or by subjecting the "modified gelatin used in the present invention" to thermal dehydration, ultraviolet ray irradiation, gamma ray irradiation, electron beam irradiation or the like. In addition, the hydrogel can also be produced by crosslinking the "modified gelatin used in the present invention" utilizing salt bridge, electrostatic interaction, hydrogen bond or hydrophobic interaction. The "modified gelatin used in the present invention" to be crosslinked needs not have a single composition. That is, taking the preferred "modified gelatin used in the present invention" described above as an example, the hydrogel produced by crosslinking a mixture of succinylated gelatin and sulfoacetylated gelatin in an arbitrary ratio using a crosslinking agent is also included in the "hydrogel used in the present invention".

In the production of the "hydrogel used in the present invention" by crosslinking the "modified gelatin used in the present invention" with the crosslinking agent, the preferred concentration scope of the "modified gelatin used in the present invention" and the crosslinking agent is from about 1% to about 20% by weight and from about 0.01% to about 1% by weight, respectively. The crosslinking reaction, which is not particularly limited, may be conducted, for example, at about 0° C. to about 40° C., preferably about 25° C. to about 30° C., for about 1 hour to about 48 hours, preferably about 12 hours to about 24 hours.

Since the "modified gelatin used in the present invention" becomes water insoluble by being crosslinked and changing into the "hydrogel used in the present invention", it will be able to exhibit the excellent effect of SDF-1 sustained release. As described above, the level of sustained release may be adjusted using properties of the "modified gelatin used in the present invention" such as the isoelectric point, modification ratio or average molecular weight. The level of sustained release may also be appropriately changed by adjusting the degree of crosslinking through adjusting the concentration of the "modified gelatin used in the present invention", the concentration of the crosslinking agent, and/or the reaction conditions of crosslinking (for example, temperature or time) in the production of the "hydrogel used in the present invention".

The crosslinking of the "modified gelatin used in the present invention" may be executed by thermal dehydration. The crosslinking using thermal dehydration may be executed, for example, by flow-casting an aqueous solution (preferably about 10% by weight) of the "modified gelatin used in the present invention" on a plastic petri dish and leaving the obtain gelatin film by air-drying for about 1 hour to about 48 hours (preferably about 6 hours to about 24 hours) under reduced pressure (preferably about 10 mmHg) at a temperature of about 110° C. to about 160° C. (preferably about 120° C. to about 150° C.)

The crosslinking of the "modified gelatin used in the present invention" may also be executed by ultraviolet ray irradiation. The crosslinking by ultraviolet ray irradiation may be conducted, for example, by leaving a gelatin film obtained in the same manner as above at room temperature (preferably about 0° C. to about 40° C.) under a bactericidal lamp.

In the same manner, the crosslinking can be executed by gamma ray irradiation, electron beam irradiation or the like. Furthermore, a combination of the above crosslinking reactions may be used.

The "hydrogel used in the present invention" produced by the above methods may take any configuration. When used as an implant piece for implantation in accordance with the use of the composition of the present invention described later, the suitable configuration may be selected from granular, cylindrical, prism, sheet, disk, stick, rod, spherical, fine particulate or paste. By suitably varying the means of crosslinking, the "hydrogel used in the present invention" may be produced in the form of granular, cylindrical, prism, sheet, disk, stick, rod, spherical, fine particulate or paste. The "hydrogel used in the present invention" obtained by the crosslinking reaction can be formulated as a sponge-like formed article by freeze-drying.

The method for producing the "hydrogel used in the present invention" having a fixed form as described above will be described in further detail. For example, the "hydrogel used in the present invention" in the form of cylinder, prism, sheet or disk may be produced by addition of an aqueous solution of a crosslinking agent to an aqueous solution of the "modified gelatin used in the present invention" or by addition of an aqueous solution of the "modified gelatin having a carboxyl group and/or a sulfo group" to an aqueous solution of the crosslinking agent and placing the solutions into a template of a desired shape for crosslinking. Furthermore, it may also be produced by pre-forming an aqueous solution of the "modified gelatin used in the present invention" into a gel in a template and then adding an aqueous solution of a crosslinking agent thereto. The addition of an aqueous solution of a crosslinking agent may be conducted after drying the gel. The crosslinking reaction may be terminated by, for example, contact with a low molecular substance having an amino group such as ethanolamine or glycine or by addition of an aqueous solution having a pH of 2.5 or less. Reagents (the crosslinking agent or the low molecular substance) used in the reaction may be removed from the resulting "hydrogel used in the present invention" by washing the hydrogel with, for example, distilled water, ethanol, 2-propanol, acetone, or the like.

The spherical or granular "hydrogel used in the present invention" may be produced, for example, by adding an aqueous solution of the "modified gelatin used in the present invention" to an apparatus wherein a three-mouthed round-bottom flask is equipped with a fixed stirring motor (for example, manufactured by Shinto Scientific Co., Ltd., three-one motor, EYELA mini D.C. stirrer) and Teflon® stirring propeller and fixed together, adding an oil such as olive oil thereto, stirring the mixture at a speed of about 200 rpm to about 600 rpm to give a W/O emulsion, and then adding an aqueous solution of a crosslinking agent thereto, or dropping a previously pre-emulsified aqueous solution of the "modified gelatin used in the present invention" in olive oil (for example, using a vortex mixer (Advantec TME-21), a homogenizer or polytron (PT10-35)) to olive oil, preparing a fine particulate W/O emulsion, then adding an aqueous solution of the crosslinking agent thereto, thereby to allow for a crosslinking reaction, recovering a hydrogel fraction by centrifugation, thereafter washing the fraction with, for example, acetone or ethyl acetate, and immersing in, for example, 2-propanol, ethanol or the like to terminate the crosslinking reaction. The resulting particles of the "hydrogel used in the present invention" may be further washed in sequence with 2-propanol, distilled water containing Tween 80 and distilled water, as desired. In the step above, when the particles of the "hydrogel used in the present invention" coaggregate, addition of a surfactant or ultrasonication (under cooling for about one minute or less) may be conducted. The average particle size of the obtained "hydrogel used in the present invention" may be suitably varied by adjusting the concentration of the "modified gelatin used in the present invention" during production of the particles, the volume ratio of the aqueous solution of the "modified gelatin used in the present invention" to olive oil, the stirring speed, or the like. Generally, the particle size is from about 1 μm to about 1 mm, and particles having a required size may be appropriately screened and used depending on the purposes. Furthermore, a fine particulate "hydrogel used in the present invention" having a particle size of about 20 μm or less may also be obtained by pre-emulsification.

The size of the "hydrogel used in the present invention" obtained by the above steps may be suitably adjusted as required, freeze-dried, or used after a further sterilization. The freeze-drying can be conducted, for example, by placing the "hydrogel used in the present invention" into distilled water and performing freezing in liquid nitrogen for about 30 minutes or more or for about 1 hour or more at a temperature of about −80° C. and then drying the hydrogel in a freeze-drying apparatus for about 1 day to about 3 days.

The composition of the present invention may be produced by bringing SDF-1 into contact with the "hydrogel used in the present invention". Any method of contact may be used. To give a specific example, the composition of the present invention may be produced by bringing the freeze-dried "hydrogel used in the present invention" obtained from the steps above into contact with an aqueous solution of SDF-1 to load SDF-1 in the "hydrogel used in the present invention". To give a more specific example, it may be obtained by dropping an aqueous solution of SDF-1 into the above freeze-dried "hydrogel used in the present invention", or by impregnating the "hydrogel used in the present invention" into an aqueous solution of SDF-1 to load SDF-1 in the "hydrogel used in the present invention". These operations are usually conducted at a temperature of about 4° C. to about 37° C. for about 15 minutes to about 1 hour, and preferably at a temperature of about 4° C. to about 25° C. for about 15 minutes to about 30 minutes. Through this step, the "hydrogel used in the present invention" swells, or SDF-1 is supported and fixed in the "hydrogel used in the present invention" by a physicochemical interaction.

The amount of SDF-1 supported in the "hydrogel used in the present invention" is preferably varied according to the amount of the "modified gelatin used in the present invention" used for production of the "hydrogel used in the present invention". More specifically, a preferred molar ratio relative to the "modified gelatin used in the present invention" is about $1/10,000$ to about 1, more preferably about $1/1,000$ to about $1/10$, still more preferably about $1/100$ to about $1/20$ and most preferably about $1/40$. For example, when supporting about 10 mmol to about 50 mmol of SDF-1 in the "hydrogel used in the present invention" produced using 1 mol of the "modified gelatin used in the present invention", a molar ratio relative to the "modified gelatin used in the present invention" may be about $1/100$ to about $1/20$.

The SDF-1 supported in the composition of the present invention is gradually released to the exterior as the "hydrogel used in the present invention" is decomposed in vivo. The speed of release is determined by (1) the level of decomposition and absorption of the used "hydrogel used in the present invention" in vivo, (2) the bonding strength of the "hydrogel used in the present invention" to SDF-1 in the composition of the present invention, and (3) the stability of the "hydrogel used in the present invention". As described above, the degree of in vivo sustained release of the "hydrogel used in the present invention" has been adjusted by the degree of crosslinking during preparation of the "hydrogel used in the present invention", and the degree of crosslinking can be numerically represented as the "water content ratio" as an index. Herein, the "water content ratio" means the weight percentage of water in the hydrogel relative to the weight of the "hydrogel used in the present invention" swollen in the aqueous solution of SDF-1. The degree of crosslinking in the "hydrogel used in the present invention" decreases and the degradability increases as the "water content ratio" increases. The "water content ratio" for showing the preferred sustained release effect of the composition of the present invention is, for example, preferably from about 80% by weight to about 99% by weight, more preferably from about 95% by weight to about 98% by weight, and still more preferably from about 95% by weight to about 96% by weight.

Other components may be added as desired to the composition of the present invention for improvement of stability of the "hydrogel used in the present invention" itself, stability of SDF-1, and continual SDF-1 release. Examples of other components include amino sugars or high molecular weight forms thereof, chitosan oligomers, basic amino acids or oligomers thereof or high molecular weight forms thereof, or basic polymers such as polyallylamine, polydiethylaminoethylacrylamide or polyethylenimine.

The composition of the present invention may be forulatmed into a formulation by being mixed with a pharmaceutically acceptable carrier (for example, stabilizer, preservative, solubilizer, pH adjusting agent, or thickener) as required to thereby formulate a composition for, for example, injection, oral administration, transnasal administration, transdermal administration, rectal administration or implantation. The composition of the present invention in such a formulation may be useful as a pharmaceutical preparation.

When the composition of the present invention is used as an injection, for example, the composition may be formulated as an aqueous suspension together with a dispersion medium such as a dispersant (for example, a surfactant such as Tween 80 or HCO-60, or a polysaccharide such as sodium hyaluronate, carboxymethyl cellulose, or sodium alginate), a preservative (for example, methylparaben or propylparaben), or a tonicity agent (for example, sodium chloride, mannitol, sorbitol, glucose, or proline), or an oil-based suspension together with a dispersant such as a vegetable oil such as sesame oil or corn oil, and thereby may formulate an actually usable injection solution. When used as an injective suspension, the particle size of the resulting composition is suffice as long as it is within a range where the degree of dispersion and the needle penetration properties are satisfied, for example, within a range from about 0.1 to about 300 μm, preferably from about 0.5 to about 150 μm, and more preferably from about 1 to about 100 μm in an average particle size. When the composition of the present invention is used as an injection solution, it is particularly preferred to be injective microsphere. The composition of the present invention as a injective microsphere may be injected of course into blood vessels such as veins or arteries, and also may be intramuscularly, preferably subcutaneously injected to release SDF-1 in the local sustained manner. The process for producing and method of using the microsphere may be referred to Masumi Koishi (ed.,), "Development and Application of Micro/Nano Capsules and Fine Particles," CMC Publishing, (2003) as required. Furthermore, the sustained release of a general physiologically active substance may be referred to Kohei Miyao, "Practical Drug Delivery Systems," Medicine and Drug Journal (1986) as required.

The composition of the present invention may be formulated into a sterile injection, under the totally sterile process, by sterilization using gamma rays, or addition of preservative, which is not particularly limited. By adding, for example, an excipient (for example, mannitol, sorbitol, lactose or glucose) as a suspension in addition to the above formulation for redispersion and then freeze-drying or spray drying for solidification, the composition of the present invention may be formulated into a more stable injection (a so-called freeze-dried preparation), which can be administered by addition of injectable distilled water or a suitable dispersant before use.

The composition of the present invention may be formulated into an orally-administered agent according to a known method of adding an excipient (for example, lactose, saccharose, or starch), a disintegrating agent (for example, starch or calcium carbonate), a binder (for example, starch, gum arabic, carboxymethyl cellulose, polyvinyl pyrrolidone, or hydroxypropyl cellulose) or a lubricant (for example, talc, magnesium stearate, or polyethylene glycol 6000) thereto and forming the resultant by compression, and then by coating according to a known method for flavor-masking, or enteric property or sustainability as required. Examples of the coating agent include hydroxypropylmethyl cellulose, ethyl cellulose, hydromethyl cellulose, hydropropyl cellulose, polyoxyethylene glycol, Tween 80, Pluronic F68, cellulose acetate phthalate, hydroxypropylmethyl cellulose phthalate, hydromethyl cellulose acetate succinate, Eudragit (manufactured by Rohm, West Germany: a methacrylic acid-acrylic acid copolymer), and coloring agents such as titanium oxide and red iron oxide.

The composition of the present invention may be formulated into a solid, semi-solid or liquid agent for transnasal administration according to a known method. For example, the composition of the present invention may be formulated into a solid agent for transnasal administration by itself or as a powdered composition obtained by adding or mixing of an excipient (for example, glucose, mannitol, starch, or microcrystal cellulose), or a thickening agent (for example, natural rubbers, cellulose derivatives, or acrylic acid polymers). Furthermore, the composition of the present invention may be formulated into a liquid agent for transnasal administration by preparing an oil-based or aqueous suspension according to the same operation as that for the above injection. A semi-solid agent for transnasal administration may contain an aqueous or oil-based gel agent, or an ointment. Any of the above formulations may be added with a pH adjusting agent (for example, carbonic acid, phosphoric acid, citric acid, hydrochloric acid, or sodium hydroxide), an preservative (for example, p-hydroxybenzoate ester, chlorobutane, or benzalkonium chloride) or the like.

The composition of the present invention may be formulated into an agent for rectal administration, that is to say, suppository, which is oil-based or aqueous solid, semi-solid or liquid, according to a known method. Examples of the oil base used in said composition include glycerides of higher fatty acids (for example, theobroma oil and Witepsol (Dynamite Nobel)), medium fatty acids (for example, miglyol (Dynamite Nobel)), and vegetable oils (for example, sesame oil, soybean oil, and cotton seed oil). Examples of the aqueous base include polyethylene glycol and propylene glycol, and examples of the aqueous gel base include natural rubbers, cellulose derivatives, vinyl polymers, and acrylic acid polymers.

To prepare an implantable formulation, the composition of the present invention may be formulated into various formulations by itself or by being enclosed in a biodegradable sheet according to the purpose. Examples of the formulation include a solid or semisolid formulation in the form of granular, cylindrical, prism form, sheet, disk, stick, rod, spherical, fine particulate or paste.

Furthermore, in addition to the above, the composition of the present invention may be formulated into a transdermal preparation according to a known method.

As described above, the composition of the present invention may be formulated into, for example, an injectable, oral, transnasal, transdermal, rectal or implantable formulation, preferably an injectable, transnasal, transdermal, rectal or implantable formulation, in particular, preferably an implantable or a subcutaneous microsphere injectable formulation.

Since the composition of the present invention is safe and low toxic, it may be used as a pharmaceutical preparation to mammals (for example, human, monkey, sheep, cow, pig, dog, cat, mouse, rat, or rabbit). Although the dosage of the composition of the present invention may be varied according to the duration of SDF-1 release, the subject disease, the subject animal, or the like, it is sufficient insofar as an effective dosage of SDF-1 is released in the sustained manner. For example, to fulfill a systemic pharmacological effect, the dosage of SDF-1 at one time for an adult may be suitably selected from a range of preferably from about 0.05 to about 50 mg/kg body weight, and more preferably from about 0.1 to about 30 mg/kg body weight. The dose frequency may be suitably selected from once per several weeks, once per month or once per several months (for example, 2 months, 3 months, 4 months, or 6 months). Furthermore, to fulfill a local pharmacological effect, the dosage of SDF-1 at one time per an adult may be suitably selected from a range of preferably from about 0.01 to about 10 mg/kg body weight, and more preferably from about 0.1 to about 1 mg/kg body weight. When the effect of a single dose is insufficient, it may be administered several times.

Since the composition of the present invention may release chemokine SDF-1 in the sustained manner for about at least 1 week, preferably about 2 weeks to about one month, more preferably about 1 to about 2 months, and still more preferably about 2 to about 3 months, it may be administered, for example, subcutaneously, intramuscularly, intravenously, intraluminally or locally into a damaged tissue, an organ site or a diseased organ, to accumulate bone marrow-derived cells, representative of vascular progenitor cells, at the administration site and thereby induce angiogenesis.

Furthermore, the composition of the present invention can induce regeneration of various tissue such as cartilage, muscle and dermal tissues.

Furthermore, the composition of the present invention may be used, based on the above working mechanism, as a pharmaceutical preparation, for treatment and/or suppression of symptom progression of various diseases, for example, ischemic disease or bone disease. Examples of the ischemic disease herein include pressure sore, dermal ulceration, mucosal membrane ulceration, wound, rejection reactions during transplantation, severe limb ischemia, ischemic heart diseases (for example, myocardial infarction, acute myocardial infarction, cardiomyopathy, cardioembolism, cardiac angina, unstable angina, coronary arteriosclerosis, and cardiac failure), peripheral arterial disease, arteriosclerosis obliterans (ASO), Buerger's disease, vascular damage, arterial occlusive disease, arterial thrombosis, systemic arterial occlusive disease, aneurysm, occlusive cerebrovascular lesion, cerebral infarction, cerebral thrombosis, cerebral embolism, stroke, cerebral hemorrhage, Moya Moya disease, cerebrovascular dementia, Alzheimer's disease, aftereffects of intracerebral hemorrhage, aftereffects of cerebral infarction, diabetic neuropathy, and hemadostenosis. Examples of the bone disease include traumatic bone fracture, stress fracture, pathological fracture (for example, osteoporosis (for example, primary osteoporosis (senile, postmenopausal, or juvenile), secondary osteoporosis (for example, hyperthyroidism or Cushing's syndrome (due to steroid administration), acromegaly, hypogonadism (for example, hypopituitarism, Klinfelter syndrome, or Turner syndrome), dysosteogenesis, hypophosphatasia, homocystinuria, or immobilization osteoporosis)), osteomalacia, malignant tumor, multiple myeloma, osteogenesis imperfecta congenital, bone cysts, suppurative osteomyelitis, marble bone disease, or fractures associated with trophopathy). In the present invention, the "treatment" means to lead disease condition to curing and the "suppress of symptom progression" means to stop or suppress the progression of disease condition.

EXAMPLES

The present invention will be described in detail hereinafter, but is not limited thereto.

Example 1

(1) Production of Succinylated Gelatin

A dehydrated dimethyl sulfoxide (4.5 g) solution of succinic anhydride (Nacalai Tesque: #324-07) (27 mg) was dropped with stirring into a dehydrated dimethyl sulfoxide (14 g) solution of bovine bone-derived alkali-treated pI5 gelatin (Nitta Gelatin) (2 g) and the mixture was stirred at 37° C. for 1 hour. The reaction liquid (final concentration of gelatin: 9.76% by weight, final concentration of succinic anhydride: 0.13% by weight) was placed in a dialysis membrane (Viskase Companies, Inc.: #UC30-32-100) and dialyzed for 3 days using pure water as a solvent. After dialysis, the reaction liquid was placed on a tray, frozen at −80° C. and freeze-dried in a freeze-drying apparatus (EYELA: #FDU-830) to obtain succinylated gelatin having the following physical property values. The resulting succinated gelatin was stored under sealed conditions at 4° C.
<Physical Property Values>
Modification Ratio (introduction ratio of succinyl groups): 25 to 30%
Isoelectric Point: 4.72 to 4.74
Average Molecular Weight: about 100,000
(2) Production of Sulfoacetylated Gelatin MES buffer solution of sulfoacetic acid (Aldrich: #242802) (4.44 g) was dropped with stirring into MES (2-morpholino ethanesulfonic acid monohydrate: DOJINDO: #349-01623) buffer (0.1 M, pH 5.0, 38 g) solution of bovine bone-derived alkali-treated pI5 gelatin (Nitta Gelatin) (2 g). An aqueous solution of sodium hydroxide (5 N) was used to adjust the pH of the reaction liquid to 5.0. EDC hydrochloride salt (Nacalai Tesque: #15022-44) (0.364 g) was added to adjust the total amount of the MES buffer to 60 mL and then the solution was stirred at 37° C. for 18 hours. The reaction liquid (final concentration of gelatin: 9.76% by weight, final concentration of succinic anhydride: 0.13% by weight) was placed in a dialysis membrane (Viskase Companies, Inc.: #UC30-32-100), and dialyzed for 3 days using pure water as a solvent. After dialysis, the reaction liquid was placed on a tray, frozen at −80° C. and freeze-dried in a freeze-drying apparatus (EYELA: #FDU-830) to obtain sulfoacetylated gelatin having the following physical property values. The resulting sulfoacetylated gelatin was stored under sealed conditions at 4° C.
<Physical Property Values>
Modification Ratio (introduction ratio of sulfoacetyl groups): 20%
Isoelectric Point: 4.57
Average Molecular Weight: about 100,000

Example 2

(1) Production of Succinated Gelatin Hydrogel

An aqueous solution of sodium hydroxide (5 N) was used to adjust the pH of an aqueous solution (22.8 g) of succinylated gelatin (1.2 g) produced in Example 1(1) to 5.0, and then each 10 mL of the solution was poured into centrifugation tubes. 45 μL of 25% glutaraldehyde aqueous solution (Nacalai Tesque: #17003-92) was added to each centrifugation tube and stirred gently for 30 seconds. Each 5 mL of the reaction liquid was dispensed onto a balance dish M (Bio-Bik), covered with aluminum foil and left at room temperature for 30 minutes, and then gelatinized by performing crosslinking at 4° C. for 12 hours. The removed gel was placed in an aqueous solution (0.1 M, 500 mL) of glycine (Nacalai Tesque: #17141-95) and the crosslinking reaction was stopped by shaking the mixture at room temperature for 1 hour. For washing, the aqueous glycine solution was replaced with pure water. The resultant was shaken at room temperature for 1 hour. The above operation was repeated 3 times in order to obtain a succinylated gelatin hydrogel having the following physical property values. The resulting gel was frozen at −80° C. and freeze-dried in a freeze-drying apparatus (EYELA: #FDU-830). Sterilization was conducted using ethylene oxide gas and the sterilized freeze-dried body of the succinylated gelatin hydrogel was stored under sealed conditions at 4° C. Measurement of the water content ratio (% by weight) may be conducted using the method described in Biomaterials, 19, 1781-9 (1998).
<Physical Property Values>
Water Content Ratio: 97 to 98%
(2) Production of Sulfoacetylated Gelatin Hydrogel An aqueous solution of sodium hydroxide (1 N) was used to adjust the pH of an aqueous solution (22.8 g) of sulfoacetylated gelatin (1.2 g) produced in Example 1(2) to 5.0, and then each 10 mL of the solution was poured into centrifugation tubes. 40 μL of 25% aqueous glutaraldehyde solution (Nacalai Tesque: #17003-92) was added to each centrifugation tube and stirred gently for 30 seconds. Each 5 mL of the reaction liquid was poured onto a balance dish M (Bio-Bik), covered with aluminum foil and left at room temperature for 30 minutes and gelatinized by performing crosslinking at 4° C. for 12 hours. The removed gel was placed in an aqueous solution (0.1 M, 500 mL) of glycine (Nacalai Tesque: #17141-95) and the crosslinking reaction was stopped by shaking the mixture at room temperature for 1 hour. For washing, the aqueous glycine solution was replaced with pure water. The resultant was shaken at room temperature for 1 hour. The above operation was repeated 3 times in order to obtain a sulfoacetylated gelatin hydrogel having the following physical property values. The resulting gel was frozen at −80° C., freeze-dried in a freeze-drying apparatus (EYELA: #FDU-830) and steriled using ethylene oxide gas and then the sterilized freeze-dried sulfoacetylated gelatin hydrogel was stored under sealed conditions at 4° C. The water content ratio (% by weight) may be measured using the method described in Biomaterials, 19, 1781-9 (1998).
<Physical Property Values>
Water Content Ratio: 98%
(3) Production of Other Gelatin Hydrogels Various sterilized freeze-dried gelatin hydrogels were prepared according to performing the same operations as in Example 2(1) or 2(2) using starting materials such as decylated gelatin, alkali-treated gelatin, acid-treated gelatin, ethylenediamine-containing gelatin and spermine-containing gelatin produced according to known methods.

Example 3

Production of SDF-1/Hydrogel Complex (Preparation for Implantable Formulation)

An SDF-1/hydrogel complex (implantable formulation) was prepared by dropping SDF-1 (human genetically recombinant SDF-1α, R&D Systems Inc.) (20 μL) isotope ($^{125}$I)-labeled by a chloramine T method onto various freeze-dried gelatin hydrogels (2 mg) produced in Examples 2(1), 2(2) and 2(3) and then leaving the resultant at 4° C. for 12 hours.

Example 4

Investigation of Sustained Release Action by Implantation in Murine Dorsal Skin

Various SDF-1/hydrogel complexes produced in Example 3 were implanted in the dorsal skin of a mouse and the gel was harvested after 24 hours. The residual amount of SDF-1 was calculated by measuring the radioactivity remaining in the gel.
<Results>

The results are shown in FIG. 1. With respect to sustained release of SDF-1, the residual ratio after 24 hours of implantation show that the sulfoacetylated gelatin hydrogel and the succinylated gelatin hydrogel demonstrate excellent results in comparison with other gelatin hydrogels. In FIG. 1, the symbols mean as follows:

sulfo: SDF-1/sulfoacetylated gelatin hydrogel complex;
succ: SDF-1/succinylated gelatin hydrogel complex;
C11: SDF-1/decylated gelatin hydrogel complex;
pI=5: SDF-1/alkali-treated gelatin hydrogel complex;
pI=9: SDF-1/acid-treated gelatin hydrogel complex E50: SDF-1/ethylenediamine-containing gelatin hydrogel complex; and
SM50: SDF-1/spermine-containing gelatin hydrogel complex.

Example 5

Figure 2:
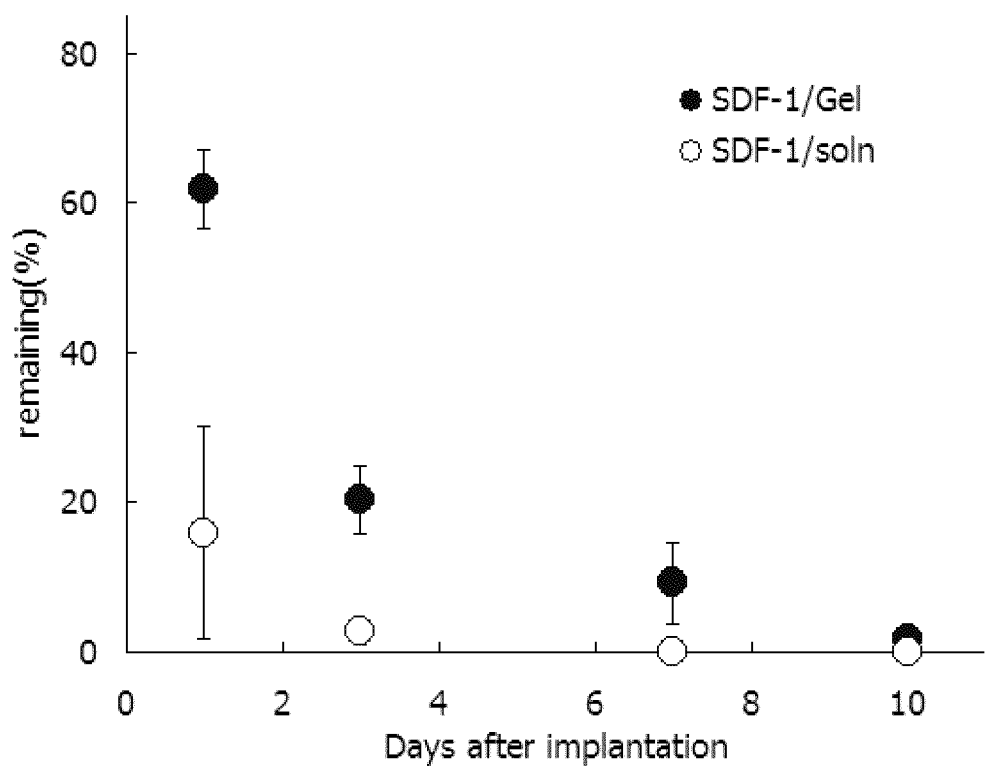
FIG. 2 shows the sustained release of SDF-1 from a succinylated gelatin hydrogel.

Investigation of Sustained Release Action (Temporal Change) by Implantation in Murine Dorsal Skin The SDF-1/succinylated gelatin hydrogel complex produced in Example 3 was implanted in the dorsal skin of a mouse and the gel and the peripheral tissue were harvested over time. The residual amount of SDF-1 was calculated by measuring the radioactivity remaining in the gel.
<Results>
The results are shown in FIG. 2. In the group of the SDF-1/succinylated gelatin hydrogel complex, SDF-1 has been released even after 7 to 10 days from implantation, and the group exhibited the excellent sustained release activity in comparison to the group in which only an SDF-1 aqueous solution was administered. In FIG. 2, the symbols mean as follows:
SDF-1/Gel: SDF-1/succinylated gelatin hydrogel complex; and
SDF-1/soln: SDF-1aqueous solution.

Example 6

Investigation of Angiogenic Induction by Implantation in Murine Dorsal Skin

Figure 3:
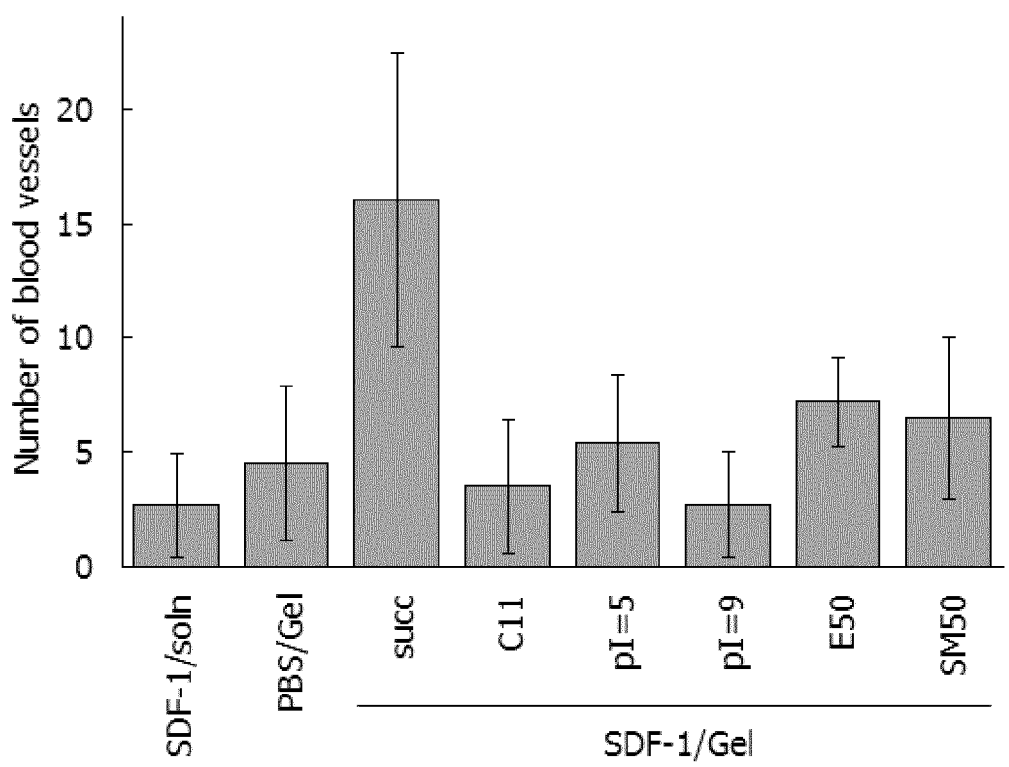
FIG. 3 shows the angiogenesis-inducing effect of administration of a succinylated gelatin hydrogel containing SDF-1.

A chamber provided with a glass viewing port was mounted in the dorsal dermal tissue of a mouse. 6 mm diameter of circular dermal wound was created in the skin leaving the subcutaneous tissue. Various non-radioactively-labeled SDF-1 (corresponding to 5 µm)/gelatin hydrogel complexes produced separately according to performing the same operations as in Example 3 were transplanted and left. The subcutaneous tissue was observed over time by a microscope and the number of induced blood vessels was counted.
<Results>
The results are shown in FIG. 3. In the group on the SDF-1/gelatin hydrogel complex, high levels of angiogenic induction were observed on 4 days after implantation in comparison to groups of other hydrogels. The angiogenic inductions of groups of other hydrogels were of the same level as the group in which an SDF-1 aqueous solution was administered or the group in which only a hydrogel was administered (no SDF-1). In FIG. 3, the symbols mean as follows:
SDF-1/soln: SDF-1 aqueous solution;
PBS/Gel: hydrogel only (use of PBS (phosphate buffer solution) as a substitute for SDF-1);
succ: SDF-1/succinylated gelatin hydrogel complex;
C11: SDF-1/decylated gelatin hydrogel complex;
pI=5: SDF-1/alkali-treated gelatin hydrogel complex;
pI=9: SDF-1/acid-treated gelatin hydrogel complex;
E50: SDF-1/ethylenediamine-containing gelatin hydrogel complex;
SM50: SDF-1/spermine-containing gelatin hydrogel complex; and
SDF-1/Gel: SDF-1/various gelatin hydrogel complex.

Example 7

Investigation of Accumulating Action of Vascular Progenitor Cells Using Chimeric Mouse Bone marrow cells were extracted from a GFP-expressing mouse and the cells were transplanted into a normal mouse irradiated with X-rays to thereby prepare a chimeric mouse. The non-radioactively-labeled SDF-1 (corresponding to 5 µm)/succinylated gelatin hydrogel complex produced separately according to performing the same operations as in Example 3 were implanted in said mouse and the number of CD34 positive cells (vascular progenitor cells) was counted from the GFP positive cells accumulated on the gel periphery 48 hours later.

The accumulation of vascular progenitor cells can be evaluated by measuring the level of expression of SDF-1 receptor, CXCR4, in the tissue according to a known PCR method or a known northern blot method.
<Results>
In the group in which the SDF-1/succinylated gelatin hydrogel complex was administered, the CD34 positive cells (vascular progenitor cells) significantly increased in comparison to the group in which only SDF-1 aqueous solution was administered. This effect is due to the fact that locally accumulated angiogenic cells increased due to sustained release of SDF-1 and thereby resulted in angiogenic enhancement.

Example 8

Investigation of Osteoblastic Activity of SDF-1/Succinylated Gelatin Hydrogel Complex A succinylated gelatin hydrogel having a water content ratio of 97.9% is impregnated with SDF-1 aqueous solution and then the resultant is implanted into a wound (20 mm) prepared in the ulna of a NZW rabbit (2.5 to 3 kg, male). The implanted complex is harvested 6 weeks later, and the bone density is measured using pQCT and then cross-sectional hematoxylin-eosin stained slices are prepared.

All publications, patents and patent applications cited in the present specification are hereby incorporated by reference herein in their entirety.

INDUSTRIAL APPLICABILITY

The sustained release composition containing (1) SDF-1 and (2) a hydrogel containing modified gelatin having a carboxyl group and/or a sulfo group disclosed in the present invention is safe and useful as a pharmaceutical preparation by being formulated into various forms. Since the composition can release chemokine SDF-1 in the sustained manner in vivo, the composition may be, for example, injected, administered transnasally, transdermally, rectally, or implanted to thereby be able to induce angiogenesis or induce regeneration of various tissues such as cartilage, muscle and dermal tissues. Furthermore, the composition may, for example, treat and/or suppress symptom progression of ischemic disease or bone disease.

The invention claimed is:
1. A sustained released composition containing SDF-1 and a hydrogel containing a modified gelatin, wherein the modified gelatin is a gelatin including succinylated amino groups, having a ratio of said succinylated amino groups to all amino groups in said modified gelatin of about 15% to about 30%, and having an average molecular weight of about 90,000 to about 110,000.

2. The sustained release composition according to claim 1, wherein the modified gelatin has an isoelectric point of about 4.5 to about 5.0.

3. The sustained release composition according to claim 1, wherein the ratio of the succinated amino groups to all amino groups in said modified gelatin is about 25% to about 30%.

4. The sustained release composition according to claim 3, wherein the modified gelatin has an isoelectric point of 4.72 to 4.74.

5. The sustained release composition according to claim 1, wherein said sustained release composition contains SDF-1 and modified gelatin in a molar ratio of about 0.01 to about 0.05.

6. The sustained release composition according to claim 1, wherein SDF-1 is SDF-1α, SDF-1β or a mixture thereof in an arbitrary ratio.

7. The sustained release composition according to claim 1, wherein said composition is formulated for injection, transnasal administration, transdermal administration, rectal administration or implantation.

8. The sustained release composition according to claim 7, wherein said composition is formulated for implantation.

9. The sustained release composition according to claim 8, wherein said composition has a water content ratio of about 95% to about 98%.

10. The sustained release composition according to claim 8, wherein SDF-1 is released over at least 1 week.

11. The sustained release composition according to claim 10, wherein SDF-1 is released over about 1 month to about 2 months.

12. The sustained release composition according to claim 7, wherein the composition is in microsphere form.

13. The sustained release composition according to claim 1 for treatment and/or suppression of symptom progression of ischemic disease or bone disease.

14. A pharmaceutical preparation comprising the sustained release composition according to claim 1.

15. The sustained release composition according to claim 9, wherein said composition has a water content ratio of about 95% to about 96%.

16. The sustained release composition according to claim 12, wherein said composition is formulated for subcutaneous injection.

17. A method for sustained releasing SDF-1 in vivo, comprising administering an effective amount of the pharmaceutical preparation according to claim 14 to a mammal.

18. A method of treatment and/or suppression of symptom progression of ischemic disease or bone disease comprising administering an effective amount of the pharmaceutical preparation according to claim 14 to a subject in need thereof.

* * * * *